United States Patent
Ci

(10) Patent No.: US 10,335,447 B2
(45) Date of Patent: Jul. 2, 2019

(54) SOLID BEVERAGE FOR CONDITIONING QI DEFICIENCY CONSTITUTION AND METHOD FOR PRODUCING THE SAME

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 0 days.

(21) Appl. No.: 15/876,208

(22) Filed: Jan. 22, 2018

(65) Prior Publication Data

US 2019/0160136 A1    May 30, 2019

(30) Foreign Application Priority Data

Nov. 30, 2017 (CN) .......................... 2017 1 1240174

(51) Int. Cl.

| | | |
|---|---|---|
| *A61K 36/00* | (2006.01) | |
| *A61K 36/8967* | (2006.01) | |
| *A61K 36/076* | (2006.01) | |
| *A61K 36/725* | (2006.01) | |
| *A61K 36/77* | (2006.01) | |
| *A61K 36/752* | (2006.01) | |
| *A61K 36/8945* | (2006.01) | |
| *A61K 36/48* | (2006.01) | |
| *A61K 47/36* | (2006.01) | |
| *A61K 47/18* | (2017.01) | |
| *A61K 9/00* | (2006.01) | |
| *A23L 2/39* | (2006.01) | |
| *A23L 2/60* | (2006.01) | |
| *A23L 33/105* | (2016.01) | |
| *A23L 33/125* | (2016.01) | |
| *A61P 43/00* | (2006.01) | |
| *A61K 36/88* | (2006.01) | |

(52) U.S. Cl.
CPC ............ *A61K 36/8967* (2013.01); *A23L 2/39* (2013.01); *A23L 2/60* (2013.01); *A23L 33/105* (2016.08); *A23L 33/125* (2016.08); *A61K 9/0095* (2013.01); *A61K 36/076* (2013.01); *A61K 36/48* (2013.01); *A61K 36/725* (2013.01); *A61K 36/752* (2013.01); *A61K 36/77* (2013.01); *A61K 36/88* (2013.01); *A61K 36/8945* (2013.01); *A61K 47/183* (2013.01); *A61K 47/36* (2013.01); *A61P 43/00* (2018.01); *A23V 2002/00* (2013.01); *A61K 2236/15* (2013.01)

(58) Field of Classification Search
None
See application file for complete search history.

*Primary Examiner* — Qiuwen Mi

(74) *Attorney, Agent, or Firm* — Gokalp Bayramoglu

(57) ABSTRACT

A solid beverage for conditioning qi deficiency constitution. The solid beverage includes the following components in parts by weight: 25-60 parts of *polygonatum odoratum*, 30-52 parts of fuling, 28-53 parts of Chinese dates, 26-48 parts of arillus longan, 15-34 parts of orange peels, 30-53 parts of *lilium brownii*, 27-52 parts of Chinese yam, 26-56 parts of hyacinth bean, 37-77 parts of dextrin, 15-43 parts of maltodextrin, 18-50 parts of soluble starch and 0.1-0.38 parts of aspartame.

3 Claims, 2 Drawing Sheets

US 10,335,447 B2

SOLID BEVERAGE FOR CONDITIONING QI DEFICIENCY CONSTITUTION AND METHOD FOR PRODUCING THE SAME

CROSS REFERENCE TO RELATED APPLICATIONS

This application is based upon and claims priority to Chinese patent application no. CN2017112401745, filed on Nov. 30, 2017, the entire content of which is incorporated herein by reference.

TECHNICAL FIELD

The present invention relates to the field of health foods, and particularly to a solid beverage for conditioning qi deficiency constitution and a method for producing the same.

BACKGROUND

In *Classification and Determination of Constitution in Traditional Chinese Medicine*, the China Association of Chinese Medicine classifies body constitutions of the human body into nine types, i.e., yin-yang harmony constitution, yang deficiency constitution, yin deficiency constitution, qi deficiency constitution, phlegm-dampness constitution, damp-heat constitution, qi stagnation constitution, blood stasis constitution and allergic constitution, most of which are sub-healthy states.

The qi deficiency constitution means that, when internal organs of the human body are dysfunctional and transformation and generation of qi are insufficient, manifestations of qi deficiency would easily occur, which are usually represented by faint low voice, emaciation of the body or overweight, pale complexion, shortness of breath and unwillingness to speak, lassitude, body fatigue and weakness, spontaneous perspiration which is especially more serious when in movement, pale red tongue with teeth prints and with white tongue coating, and weak pulse, diseases are caused due to various causes, different symptoms are seen due to the difference in qi-deficient parts such as heart, lung, spleen and kidney. The tendency of morbidity is: being susceptible to common cold and visceroptosis, usually having weakened immune systems and having slow recovery from illness. For this, qi tonifying and qi nourishing are taken as the general therapeutic principle, and prescriptions for tonifying viscera are selected on the basis of differentiation of diseases according to pathological changes of the viscera and their interrelations.

The qi deficiency constitution is formed mainly because native endowment is deficient and after long-term eating disorder, emotional disorder, long illness and fatigue, oldness and weakness cause heart, lung, spleen and kidney damages. Since heart governs blood and vessels, lung dominates qi throughout the body, kidney stores vigor, and spleen and stomach are "source of engendering transformation of qi", the qi deficiency constitution will easily develop symptoms that the effect of promoting blood running is reduced, transformation and generation of qi in the body are insufficient, and the functions of the body in preventing the invasion of exogenous pathogenic factors, protecting the superficies of the body, and maintaining the positions of the internal organs are decreased.

Such sub-healthy constitution as qi deficiency constitution belongs to chronic diseases and has a relatively long disease course, and requires a long-term medication and gradual conditioning, in order to achieve the effects of tonifying qi and nourishing qi. The dosage forms commonly used in the traditional Chinese medicine are decoctions and Chinese patent medicine such as pills and the like. Decoctions usually have relatively good efficacy, but the administration thereof is complicated, and the taste thereof is poor, if the decoctions need to be administered for a long time, it is difficult for a patient to keep taking the decoctions. Moreover, the efficacy of the pills is relatively poor.

Food is the best product for human beings to prevent diseases and keep healthy. The theory that "medicine and food share a common origin" is one of the most valuable contributions made by the original Chinese medicine to human beings. It is described in the *Rites of Zhou•OEfices of the Heaven•Medicine* that "diseases are treated with the five flavors, the five grains and the five medicines", which demonstrates the physical health-care functions of food. The method of regulating body functions using the characteristics of food so as to obtain health or prevent or treat diseases is called dietary therapy. However, "therapy" is inferior to "nourishing", and food nourishing is an approach to increase resistance against diseases and enhance immunity by eating tonic food according to food nutritions in combination with the body conditions, so as to strengthen the body and prolong the life. It is described in *Prescriptions Worth a Thousand Gold* that "a physician should first know the cause of a disease to know why the disease is developed and treat the disease with food materials. Only when food materials are unable to treat the disease, can drugs be used." Thus, dietary therapy was not only the basic therapeutic approach of the physicians at that time, but also an important criterion for determining whether a physician was a great physician.

It is mentioned in the *Inner Canon of the Yellow Emperor* that "the superior physician prevents illness, the mediocre physician attends to impending illness, and the inferior physician treats actual illness", wherein the phrase "prevent illness" means taking corresponding measures to prevent the occurrence and development of diseases. The body constitution determines the health of people and determines the susceptibility to diseases. Faced with the situations that there are various diseases in modern society, the age of onset becomes lower and lower and there are more and more sub-healthy people, dietary therapy gets more and more popular with the consumers due to its advantages of being healthy and natural, and with respect to the diseases that are easy to develop, it is of great significance to develop a food product that has the functions of life nourishing and health protection, has a good taste and conditions the qi deficiency constitution, by using modern scientific technologies and methods and the theory that "medicine and food share a common origin", referring to the precious Chinese traditional life nourishing experience in combination with good accumulation of the traditional Chinese medicine on the aspect of conditioning qi deficiency constitution.

SUMMARY

The main object of the present invention is to provide a life nourishing and health protecting food product for conditioning qi deficiency constitution.

In order to achieve the above object, according to one aspect of the present invention, there is provided a solid beverage for conditioning qi deficiency constitution.

The solid beverage for conditioning qi deficiency constitution according to the present invention comprises the following components in parts by weight: 25-60 parts of *polygonatum odoratum*, 30-52 parts of fuling, 28-53 parts of Chinese dates, 26-48 parts of arillus longan, 15-34 parts of orange peels, 30-53 parts of *lilium brownii*, 27-52 parts of Chinese yam, 26-56 parts of hyacinth bean, 37-77 parts of dextrin, 15-43 parts of maltodextrin, 18-50 parts of soluble starch and 0.1-0.38 parts of aspartame.

Further, the solid beverage for conditioning qi deficiency constitution of the present invention comprises the following components in parts by weight: 35-50 parts of *polygonatum odoratum*, 35-45 parts of filing, 33-47 parts of Chinese dates, 30-43 parts of arillus longan, 20-29 parts of orange peels, 36-48 parts of *lilium brownii*, 33-44 parts of Chinese yam, 31-50 parts of hyacinth bean, 45-65 parts of dextrin, 20-35 parts of maltodextrin, 22-35 parts of soluble starch and 0.15-0.33 parts of aspartame.

Further, the solid beverage for conditioning qi deficiency constitution of the present invention comprises the following components in parts by weight: 40 parts of *polygonatum odoratum*, 40 parts of fuling, 40 parts of Chinese dates, 40 parts of arillus longan, 24 parts of orange peels, 40 parts of *lilium brownii*, 40 parts of Chinese yam, 40 parts of hyacinth bean, 55 parts of dextrin, 28 parts of maltodextrin, 28 parts of soluble starch and 0.22 parts of aspartame.

In order to achieve the above object, according to another aspect of the present invention, there is provided a method for producing a solid beverage for conditioning qi deficiency constitution.

The method for producing a solid beverage for conditioning qi deficiency constitution according to the present invention comprises the steps of:

(1) preparation of raw materials: subjecting Chinese yam, fuling, *polygonatum odoratum*, hyacinth bean, Chinese dates, arillus longan, *lilium brownii* and orange peels to impurity removal, cleansing, cutting and pulverization, and then mixing them for later use;

(2) decoction: decocting the mixture resulting from step (1) with water twice to obtain a traditional Chinese medicine liquid;

(3) concentration: pumping the traditional Chinese medicine liquid prepared in step (2) into an inspissator through a pipe to concentrate the same into thick paste; and (4) wet granulation: mixing and stirring dextrin, maltodextrin, soluble starch and aspartame to obtain a mixture adjuvant, adding the thick paste prepared in step (3) to the mixture adjuvant, and stirring the same for granulation.

Further, the two-time decoction process in step (2) is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction.

Further, the temperature for the concentration in step (3) is 70-80° C., and the relative density of the prepared thick paste is 1.2-1.5 at the temperature of 50° C.

Further, the wet granulation in step (4) comprises the steps of:

(4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving;

(4.3) drying: putting the sieved particles prepared from step (4.2) into a boiling dryer for drying; and (4.4) secondary sieving: carrying out secondary sieving by using a wig-wag machine.

Further, the sieve for the primary sieving is a 12-mesh sieve, and the sieve for the secondary sieving is a 10-mesh sieve.

Further, in the drying process in step (4.3), the temperature of the materials is controlled to be 70-80° C., and the moisture of the final materials is controlled to be 5% or less.

Further, after the secondary sieving, the method further comprises a particle selecting step to select particles of 10-60 meshes.

The solid beverage of the present invention is simple and convenient to prepare, the raw materials used are all medicinal materials with dual-purpose of drug and food, and the auxiliary materials used also meet the national standard GB2760-2011 (the National Food Safety Standard for Food Additive Use). Thus, the solid beverage is safe to consume and good in taste, and has certain effects on the improvement of qi deficiency constitution, and the production process thereof is suitable for industrial mass production.

BRIEF DESCRIPTION OF THE DRAWINGS

The accompanying drawings, which constitute a part of the present application, are used to provide a further understanding of the present invention, so that other features, objects and advantages of the present application become more obvious. The illustrative drawings for embodiments of the present invention and the description thereof are used to explain the present invention, rather than constitute an improper limitation on the present invention. In the drawings.

DETAILED DESCRIPTION OF THE EMBODIMENTS

Figure 1:
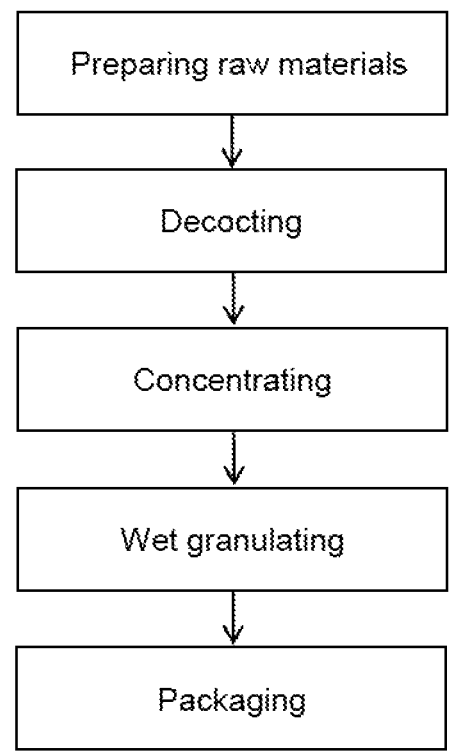
FIG. 1 is a production process of a solid beverage according to an embodiment of the present invention.

In order to enable a person skilled in the art to better understand the solutions of the present application, the technical solutions of the embodiments of the present invention will be described clearly and completely below with reference to the drawings of the embodiments of the present application. Apparently, the embodiments described are some of the embodiments of the present application, rather than all of the embodiments. All the other embodiments that are obtained by a person skilled in the art without inventive effort on the basis of the embodiments of the present application shall be covered by the protection scope of the present application.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the embodiments of the present application and the features of the embodiments can be combined with each other if there is no conflict. The present application will be described in detail below with reference to the accompanying drawings and embodiments.

The main object of the present invention is to provide a life nourishing and health protecting food product for conditioning qi deficiency constitution.

In order to achieve the above object, according to one aspect of the present invention, there is provided a solid beverage for conditioning qi deficiency constitution.

The solid beverage for conditioning qi deficiency constitution according to the present invention comprises the following components in parts by weight: 25-60 parts of *polygonatum odoratum*, 30-52 parts of fuling, 28-53 parts of Chinese dates, 26-48 parts of arillus longan, 15-34 parts of orange peels, 30-53 parts of *lilium brownii*, 27-52 parts of Chinese yam, 26-56 parts of hyacinth bean, 37-77 parts of dextrin, 15-43 parts of maltodextrin, 18-50 parts of soluble starch and 0.1-0.38 parts of aspartame.

*Polygonatum odoratum* is sweet in flavor and neutral in nature; acts on lung and stomach; has the efficacies of nourishing yin, moistening the lung, promoting the secretion of saliva or body fluid, and nourishing the stomach; and is used for yin deficiency and irritating dry cough, polydipsia and mouth dryness, and internal-heat consumptive thirst.

Fuling is sweet and light in flavor and neutral in nature; acts on heart, lung, spleen and kidney; has the efficacies of clearing damp and promoting diuresis, tonifying spleen, calming the mind; and is used for edema and scanty urine, phlegm and fluid retention, dizziness and palpitation, spleen deficiency and low food intake, loose stool and diarrhea, uneasiness, palpitation to insomnia.

Chinese dates are warm in nature and sweet in flavor; act on spleen and stomach; and have the efficacies of strengthening spleen and stomach, nourishing yin and blood, and tranquilizing by nourishing the heart.

Arillus longan is sweet in flavor and warm in nature; acts on heart and spleen; has the efficacies of invigorating heart and spleen, and nourishing the blood and tranquilization; and is used for deficiency of qi and blood, palpitation, amnesia and insomnia, blood deficiency and etiolation.

Orange peels are acrid and slightly bitter in flavor and warm in nature; act on spleen and lung; have the efficacies of regulating vital energy and regulating middle energizer, and drying dampness and resolving phlegm; and can be used for the treatment of spleen and stomach qi stagnation, abdominal fullness and distention, vomiting, or chest stuffiness, anorexia and loose stool caused by dampness turbidity blocking, however, people having yin and body fluid depletion and having endogenous excess-heat should use them with caution.

*Lilium brownii* is sweet in flavor and cold in nature; acts on heart and lung; has the efficacies of nourishing yin, moistening the lung, clearing away the heart fire and tranquilizing; and is used for yin deficiency and irritating dry cough, over-strained cough, hemoptysis, dysphoria, pavor, insomnia and dreamful sleep, and trance.

Chinese yam is sweet in flavor and neutral in nature; acts on spleen, lung and kidney; has the efficacies of tonifying spleen and nourishing stomach, promoting the secretion of saliva or body fluid and tonifying lung, and tonifying kidney and arresting seminal emission; and is used for spleen deficiency, chronic diarrhea, lung deficiency, kidney deficiency, morbid leukorrhea and frequent urination.

Hyacinth bean is sweet in flavor and slightly warm in nature; acts on spleen and stomach; has the efficacies of invigorating spleen for eliminating dampness; and is used for splenasthenic diarrhea, morbid leukorrhea and vomiting and diarrhoea caused by summer-heat dampness.

The qi deficiency constitution is formed mainly because native endowment is deficient and after long-term eating disorder, emotional disorder, long illness and fatigue, oldness and weakness cause heart, lung spleen and kidney damages. In the prescription, the Chinese yam tonifies spleen and nourishes stomach, promotes the secretion of saliva or body fluid and tonifies lung, and tonifies kidney and arrests seminal emission, fuling clears damp and promotes diuresis, tonifies spleen, calms the mind and tranquilizes the mind, *polygonatum odoratum* nourishes yin to moisten dryness and helps produce saliva and slakes thirst, hyacinth bean invigorates spleen for eliminating dampness and tonifies spleen qi so as to help the transportation, the Chinese dates nourish spleen and stomach, invigorate spleen-stomach and replenish qi, nourish blood for tranquilization, arillus longan vigorates qi and replenishes the blood, tranquilizes and sedate the mind, nourishes blood and prevents abortion, *lilium brownii* nourishes yin, moistens the lung, clears away the heart fire and tranquilizes the mind, and orange peels can be used for the treatment of spleen and stomach qi stagnation, abdominal fullness and distention. The treatment for qi deficiency constitution generally takes the principle of tonifying qi and conditioning the body. In the prescription, *polygonatum odoratum* and *lilium brownii* are used for nourishing yin to moisten dryness, and helping produce saliva and slaking thirst; the Chinese yam can tonify spleen and nourish stomach, promote the secretion of saliva or body fluid and tonify lung, and tonify kidney and arrest seminal emission; fuling and hyacinth bean tonify spleen qi so as to help the transportation; the Chinese dates nourish spleen and stomach to replenish qi with the dietary water and grains. Arillus longan invigorates heart and spleen, and nourishes the blood and tranquilizes the mind; orange peels regulate qi-flowing for harmonizing stomach to make all the medicinal materials tonify without causing stagnation. In addition, dextrin, maltodextrin and aspartame, on the one hand, can give play to medicinal effect and balance the nutritional ingredients, and on the other hand, can be used for flavoring.

As shown in FIG. 1, the method for producing a solid beverage for conditioning qi deficiency constitution comprises the steps of:

(1) preparation of raw materials: subjecting Chinese yam, fuling, *polygonatum odoratum*, hyacinth bean, Chinese dates, arillus longan, *lilium brownii* and orange peels to impurity removal, cleansing, cutting and pulverization, and then mixing them for later use, wherein the proportion of each raw material provided in the present invention is used herein;

(2) decoction: decocting the mixture resulting from step (1) with water twice to obtain a traditional Chinese medicine liquid:

(3) concentration: pumping the traditional Chinese medicine liquid prepared in step (2) into an inspissator through a pipe to concentrate the same into thick paste;

(4) wet granulation: mixing and stirring dextrin, maltodextrin, soluble starch and aspartame to obtain a mixture adjuvant, adding the thick paste prepared in step (3) to the mixture adjuvant, and stirring the same for granulation; and (5) packaging: subjecting the product resulting from the wet granulation to the packaging step to obtain a finished product.

The purpose of step (1) is to remove fat from the seed medicinal materials, pulverize the resultant seed medicinal materials and pass them through a 2-mesh sieve; the rhizomatic medicinal materials contain cellulose, and are rich in starch, and cutting or pulverization extraction can effectively retain the target ingredients thereof, and prevent polysaccharide swelling; and cleansing can remove impurities and soil, and effectively reduce the residuals of pollutants such as heavy metals and pesticides.

The two-time decoction process in step (2) is carried out as follows: the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction.

The temperature for the concentration in step (3) is 70-80° C., and the relative density of the prepared thick paste is 1.2-1.5 at the temperature of 50° C. The low-temperature evaporation can effectively reduce the decomposition of thermosensitive components, such as citric acid, malic acid, oxalic acid and other organic acids, and leads to high concentration efficiency without discharge of solvent steam, which facilitates evaporation, and is pollution-free to the environment, as it is carried out in an airtight space.

Figure 2:
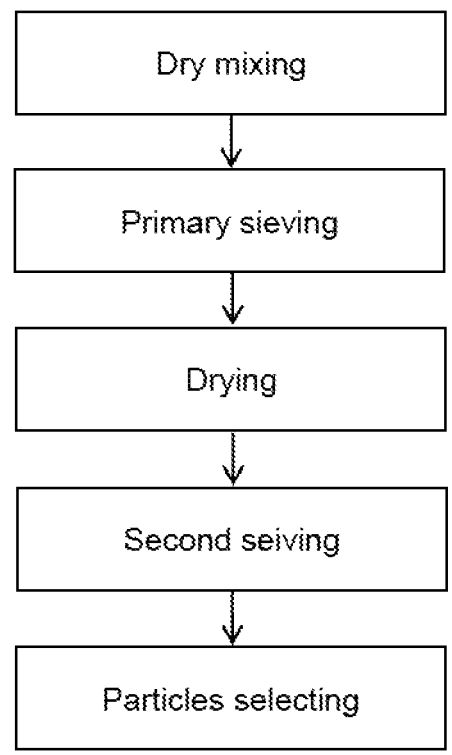
FIG. 2 is the specific steps of wet granulation in the production process of the solid beverage according to an embodiment of the present invention.

As shown in FIG. 2, the wet granulation in step (4) comprises the steps of:

(4.1) dry mixing: putting dextrin, maltodextrin, soluble starch and aspartame into an efficient mixer-granulator for mixing and stirring for 15 minutes to obtain a mixture adjuvant, wherein the proportion of each raw material provided in the present invention is used herein;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving, wherein stirring granulation can preferably prevent separation of the components, and since segregation phenomenon can easily occur due to the existence of differences in the particle size and density of the mixed extract components, granulation not only can effectively solve this problem, but also can remarkably improve the solubility.

(4.3) drying: putting the sieved particles prepared from step (4.2) into a boiling dryer for drying, wherein fluidized drying can effectively control the particle size distribution and control the product moisture; and (4.4) secondary sieving: carrying out secondary sieving by using a wig-wag machine, wherein by means of the secondary sieving, it is possible to control the particle distribution, bulk density and compactness.

In the above steps, the sieve for the primary sieving is a 12-mesh sieve, and the sieve for the secondary sieving is a 10-mesh sieve.

In the drying process in the above step (4.3), the temperature of the materials is controlled to be 70-80° C., and the moisture of the final materials is controlled to be 5% or less. In this step, pot turning can be frequently carried out according to the drying condition of the materials, so that the final material moisture meets the requirements.

On the basis of the implementation modes above, after the secondary sieving, the method further comprises a particle selecting step to select particles of 10-60 meshes. By means of particle selection, it is possible to improve the appearance and uniformity of the product particles. In practice, after the completion of the particle selection, it is feasible to make a record and tag the product to indicate the product name, the lot number, the specification, the net weight, the production date, the post name and the responsible person, fill in the equipment receipt, and transfer the product into an intermediate station.

Embodiment 1

The solid beverage for conditioning qi deficiency constitution comprises the following components in parts by weight: 25 parts of *polygonatum odoratum,* 30 parts of fuling, 28 parts of Chinese dates, 26 parts of arillus longan, 15 parts of orange peels, 30 parts of *lilium brownii,* 27 parts of Chinese yam, 26 parts of hyacinth bean, 37 parts of dextrin, 15 parts of maltodextrin, 18 parts of soluble starch and 0.1 parts of aspartame.

The production method thereof is as follows:

(1) preparation of raw materials: subjecting Chinese yam, filing, *polygonatum odoratum,* hyacinth bean, Chinese dates, arillus longan, *lilium brownii* and orange peels to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction:

(3) concentration: pumping the traditional Chinese medicine liquid prepared in step (2) into an inspissator through a pipe to concentrate the same into thick paste, wherein the temperature for the concentration is 70° C., and the relative density of the prepared thick paste is 1.2 at the temperature of 50° C.:

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 70° C., and the moisture of the final materials is controlled to be 5%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormality, the bagged particles are sealed and stored in a clean container, with the product name, the lot number, the number, the date and the like indicated for later use; the reference loading amount is 8 g per bag, and the loading limit is 8 g/bag±5%.

Embodiment 2

The solid beverage for conditioning qi deficiency constitution comprises the following components in parts by weight: 60 parts of *polygonatum odoratum,* 52 parts of fuling, 53 parts of Chinese dates, 48 parts of arillus longan, 34 parts of orange peels, 53 parts of *lilium brownii,* 52 parts of Chinese yam, 56 parts of hyacinth bean, 77 parts of dextrin, 43 parts of maltodextrin, 50 parts of soluble starch and 0.38 parts of aspartame.

The production method thereof is as follows:

(1) preparation of raw materials: subjecting Chinese yam, fuling, *polygonatum odoratum*, hyacinth bean, Chinese dates, arillus longan, *lilium brownii* and orange peels to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 80° C., and the relative density of the prepared thick paste is 1.5 at the temperature of 50° C.

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve:

(4.3) drying: putting the sieved particles prepared from step (4.2) into a boiling dryer for drying, wherein the temperature of the materials is controlled to be 80° C., and the moisture of the final materials is controlled to be 3%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormality, the bagged particles are sealed and stored in a clean container, with the product name, the lot number, the number, the date and the like indicated for later use; the reference loading amount is 8 g per bag, and the loading limit is 8 g/bag±5%.

Embodiment 3

The solid beverage for conditioning qi deficiency constitution comprises the following components in parts by weight: 35 parts of *polygonatum odoratum,* 35 parts of fuling, 33 parts of Chinese dates, 30 parts of arillus longan, 20 parts of orange peels, 36 parts of *lilium brownii,* 33 parts of Chinese yam, 31 parts of hyacinth bean, 45 parts of dextrin, 20 parts of maltodextrin, 22 parts of soluble starch and 0.15 parts of aspartame.

The production method thereof is as follows:

(1) preparation of raw materials: subjecting Chinese yam, fuling, *polygonatum odoratum*, hyacinth bean, Chinese dates, arillus longan, *lilium brownii* and orange peels to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 75° C., and the relative density of the prepared thick paste is 1.45 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve:

(4.3) drying: putting the sieved particles prepared from step (4.2) into a boiling dryer for drying, wherein the temperature of the materials is controlled to be 78° C., and the moisture of the final materials is controlled to be 3.4%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormality, the bagged particles are sealed and stored in a clean container, with the product name, the lot number, the number, the date and the like indicated for later use: the reference loading amount is 8 g per bag, and the loading limit is 8 g/bag±5%.

Embodiment 4

The solid beverage for conditioning qi deficiency constitution comprises the following components in parts by weight: 50 parts of *polygonatum odoratum*, 45 parts of fuling, 47 parts of Chinese dates, 43 parts of arillus longan, 29 parts of orange peels, 48 parts of *lilium brownii*, 44 parts of Chinese yam, 50 parts of hyacinth bean, 65 parts of dextrin, 35 parts of maltodextrin, 35 parts of soluble starch and 0.33 parts of aspartame.

The production method thereof is as follows:

(1) preparation of raw materials: subjecting Chinese yam, fuling, *polygonatum odoratum*, hyacinth bean, Chinese dates, arillus longan, *lilium brownii* and orange peels to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction:

(3) concentration: pumping the traditional Chinese medicine liquid prepared in step (2) into an inspissator through a pipe to concentrate the same into thick paste, wherein the temperature for the concentration is 73° C., and the relative density of the prepared thick paste is 1.33 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 72° C., and the moisture of the final materials is controlled to be 4.5%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormality, the bagged particles are sealed and stored in a clean container, with the product name, the lot number, the number, the date and the like indicated for later use; the reference loading amount is 8 g per bag, and the loading limit is 8 g/bag±5%.

Embodiment 5

The solid beverage for conditioning qi deficiency constitution comprises the following components in parts by weight: 40 parts of *polygonatum odoratum*, 40 parts of filing, 40 parts of Chinese dates, 40 parts of arillus longan, 24 parts of orange peels, 40 parts of *lilium brownii*, 40 parts of Chinese yam, 40 parts of hyacinth bean, 55 parts of dextrin, 28 parts of maltodextrin, 28 parts of soluble starch and 0.22 parts of aspartame.

The production method thereof is as follows:

(1) preparation of raw materials: subjecting Chinese yam, fuling. *polygonatum odoratum*, hyacinth bean, Chinese dates, arillus longan, *lilium brownii* and orange peels to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 77° C., and the relative density of the prepared thick paste is 1.4 at the temperature of 50° C.:

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 76° C., and the moisture of the final materials is controlled to be 3.8%0;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormality, the bagged particles are sealed and stored in a clean container, with the product name, the lot number, the number, the date and the like indicated for later use; the reference loading amount is 8 g per bag, and the loading limit is 8 g/bag±5%.

Experimental Example 1

The following is a test for the effects of the solid beverage for conditioning qi deficiency constitution, which is prepared according to embodiment 5 of the present invention.

The basic conditions of the cases: 100 clinical cases of qi deficiency constitution, including 50 male cases and 50 female cases. The youngest was aged 9, and the oldest was aged 72. 10 cases had allergic constitution, and often had nasal obstruction, sneezed, had a runny nose, even when they did not have a cold, and were susceptible to asthma; 15 cases easily got allergic to drugs and food; 10 cases were susceptible to smell and pollen allergies; 10 cases were prone to seasonal allergies, 25 cases were susceptible to skin urticaria, often had magenta spots and ecchymoses on the skin due to allergies, and once scratched, the skin often turned red with scratches; and 30 cases had other symptoms of qi deficiency constitution.

The usage and dosage: the solid beverage was administered 8 g each time, twice a day; and was administered after being brewed with boiling water.

The evaluation criteria for therapeutic effects:

Being cured: the clinical symptoms were completely eliminated, and normal life was restored.

Being effective: the clinical symptoms were partially eliminated, and various signs were gradually improved.

Being ineffective: the symptoms and signs were not obviously improved.

Result statistics: 53 cases were cured, the solid beverage was effective to 38 cases and ineffective to 9 cases, i.e., the solid beverage was effective to 91 cases in total, therefore the total effective rate was 91%.

Typical Cases:

Patient 1, Ms. Huang, female, 27 years old. Ms. Huang saw a doctor on Mar. 22, 2016. At that time, she often had abdominal pain, diarrhea, vomiting, or unbearably skin itching after eating food such as fish, shrimps and crabs. The physical constitution in this case was considered as qi deficiency constitution, and the solid beverage prepared in embodiment 1 was administered after being brewed with boiling water, once a day for one month. The symptoms disappeared after one month of administration.

Patient 2, Mr. Ma, male, 30 years old. Mr. Ma saw a doctor on Apr. 18, 2015. At that time, he usually had a cough, which was a dry cough without phlegm and was paroxysmal when the season changed or when he smelt unusual odors, often sneezed, and was easy to have allergic response and have skin itching in spring. He once had eczema and urticaria. The physical constitution in this case was considered as qi deficiency constitution, and the formulation in embodiment 2 was administered after being brewed with boiling water, once a day for two months. The symptoms disappeared after two months of administration, and have not relapsed so far.

Patient 3, Ms. Peng, female, 15 years old. Ms. Peng saw a doctor on May 26, 2016. She was easily allergic to pollen at that time, and had the manifestations of diarrhea and appearance of red spots and ecchymoses on the face or body. The physical constitution in this case was considered as qi deficiency constitution, and the formulation in embodiment 3 was administered after being brewed with boiling water, once a day for half a month. The symptoms disappeared after half a month of administration.

Patient 4, Mr. Mou, male, 66 years old. Mr. Mou saw a doctor on Apr. 18, 2016. At that time, he often had nasal obstruction, sneezed, had a runny nose, even when he did not have a cold, and would easily develop asthma, and these symptoms became serious when season changed. The physical constitution in this case was considered as qi deficiency constitution, and the formulation in embodiment 4 was administered, once a day for one month. The symptoms disappeared after one month of administration, and have not relapsed so far.

Experimental Example 2: Sensory Evaluation

The solid beverages prepared in embodiments 1-5 were brewed with boiling water and used as experimental groups, and the mixed liquid medicine after two decoctions prepared in the process step (2) in embodiment 5 was used a control group, three replicates of samples were collected from each of the experimental groups and the control group, and were subjected to sensory evaluation by 20 professional sensory assessors. The sensory evaluation scoring criteria are shown in table 1, and the sensory evaluation results are shown in table 2.

TABLE 1

Sensory Evaluation Scoring Criteria

| items | sensory evaluation | score |
| --- | --- | --- |
| color | relatively dark | 1 |
|  | intermediate | 5 |
|  | relatively light | 1 |
| smell | strong smell of traditional Chinese medicine | 1 |
|  | light smell of traditional Chinese medicine | 3 |
|  | medicine fragrance | 5 |
|  | relatively light | 3 |
|  | light | 1 |
| taste | bitter and astringent | 1 |
|  | relatively bitter | 3 |
|  | fragrant and sweet | 5 |
|  | relatively sweet | 3 |
|  | excessively sweet | 1 |

TABLE 1-continued

Sensory Evaluation Scoring Criteria

| items | sensory evaluation | score |
|---|---|---|
| fineness and smoothness | fine and smooth | 5 |
| | having granular sensation | 3 |
| | having a throat-scratching feeling | 1 |
| | being hard to swallow | 0 |
| overall evaluation | poor | — |
| | ordinary | — |
| | good | — |

TABLE 2

Sensory Evaluation Results of Solid Beverages

| | items | control group | experimental groups | | | | | average |
|---|---|---|---|---|---|---|---|---|
| | | | embodiment 1 | embodiment 2 | embodiment 3 | enibodimnt 4 | embodiment 5 | |
| sensory evaluation (marks) | color | 41 | 93 | 96 | 92 | 89 | 94 | 92.8 |
| | smell | 65 | 94 | 92 | 94 | 93 | 92 | 93 |
| | taste | 29 | 96 | 95 | 91 | 97 | 93 | 94.4 |
| | fineness and smoothness | 69 | 92 | 93 | 94 | 93 | 95 | 93.4 |
| | average | 51 | 93.75 | 94 | 92.75 | 93 | 93.5 | |
| overall evaluative/ person | good | 7 | 20 | 20 | 18 | 19 | 20 | 19.4 |
| | ordinary | 8 | 0 | 0 | 1 | 1 | 0 | 0.4 |
| | poor | 5 | 0 | 0 | 1 | 0 | 0 | 0.2 |

As can be known from the above experimental results, the average scores on the aspects of color, smell, taste and fineness and smoothness of the solid beverages prepared in embodiments 1 to 5 as given by the 20 professional sensory assessors are all higher than the corresponding scores given for the control group. The results show that the solid beverage provided by the present invention is greatly improved in smell and taste, as compared with the liquid medicine obtained by decocting the traditional Chinese medicine decoction pieces, moreover, sweet flavor has been added thereto, the taste and the fine and smooth feeling are greatly improved, which makes the solid beverage provided by the present invention very suitable for everyday drinking.

Experimental Example 3

In order to demonstrate that the solid beverage particles prepared by the present invention have unexpected technical effects on qi deficiency symptoms, an experiment was conducted on the product prepared by the present invention by using the qi-deficiency models prepared by a swimming strain method in combination with a controlled feeding method, so as to demonstrate the remarkable therapeutic effects of the product of the present invention, and demonstrate the prominently advantageous technical effects achieved by the present invention. The specific experiment was as follows:

1. Experimental Animals:
SD rats, half of them being male and half of them being female, with the body weight of 220-250 g.

2. Product for Experiment
the solid beverage particles prepared in embodiments 1-5 of the present application 3. Experimental Method
3.1 Preparation of Models
The rats were randomly divided into a normal group, a qi-deficiency model group, and five experimental groups of embodiments 1-5. The normal group was normally fed, and had free access to food, and the other groups were fed in a controlled manner (the feeding amount was half that of normal feeding) and conducted exhaustive swimming with the water temperature being controlled at 20° C. When the rats were swimming, they were prevented from resting by using tails to support their bodies at the bottom of the pool, swimming was conducted once a day for 14 days continuously, until they sank at the time of swimming and were still unable to return to the water surface 10 seconds later, this state was the so-called "exhausted". After the preparation of the models, the activities and the state of the rats in each group were observed. After the experiment was completed, 3% of pentobarbital sodium was administered to the rats by intraperitoneal injection for anesthesia, and 6-7 ml of blood was taken from the abdominal aorta of each rat, and was placed in a heparin anticoagulant tube for the detection of hemorrheological index.

3.2 Experimental Group-Division
The rats were randomly divided into seven groups, i.e., a normal group, a qi-deficiency model group, and experimental groups of embodiments 1-5, with ten rats in each group. The experimental groups of embodiments 1-5 of the present invention were intragastrically administered with the solid particle products prepared in embodiments 1-5 of the present application, respectively (dosage: 0.3 g/kg), and the normal group was intragastrically administered with equivalent amount of saline for 14 days continuously.

3.3 Statistical Analysis
SPSS12.0 software was used for statistics, the method of one-way analysis of variance was adopted, and analysis of variance was used for intergroup comparison.
All the data are expressed in the form of P, and P<0.05 means that the difference has the statistical significance.

4. Behavioral Study
Monitoring of the general condition: the state, activities, etc. of the model animals were observed, and scoring was carried out according to the specific characterizations thereof with reference to the scoring table 3. The scoring results are shown in table 4.

TABLE 3

Experimental Rats Biological Characterization
Semi-quantitative Scoring Observation Table

| score | state | skin and hair | color of ear and tail | stool |
|---|---|---|---|---|
| 0 | active | skin being tightly linked with fat, and | red and shiny | dry and formed stool |

TABLE 3-continued

Experimental Rats Biological Characterization
Semi-quantitative Scoring Observation Table

| score | state | skin and hair | color of ear and tail | stool |
|---|---|---|---|---|
| | | elastic, hair being bright and supple | | |
| 1 | slightly unresponsive and having reduced locomotor activity | skin being slightly flabby with reduced skin turgor, and hair being dry, yellow and matt | light red and matt | sticky, soft and formed stool |
| 2 | lassitude and sluggish | skin being flabby, fat increasing, and hair being dry or tangled | slightly white and matt | formless and loose stool with a bad smell |
| 3 | listless with weakened confrontational activities | skin being flabby, becoming obese, hair being yellow and thin, and shedding | pale or pale with cyan | greenish-brown, loose and sticky stool with a foul smell |

TABLE 4

Experimental Rats Biological
Characterization Observation Table

| groups | n | score |
|---|---|---|
| blank group | 20 | 1.38 ± 0.44 |
| model group | 20 | 4.59 ± 0.87** |
| embodiment 1 | 20 | 1.39 ± 0.33## |
| embodiment 2 | 20 | 1.45 ± 0.36## |
| embodiment 3 | 20 | 1.42 ± 0.68## |
| embodiment 4 | 20 | 1.48 ± 0.55## |
| embodiment 5 | 20 | 1.39 ± 0.57## |

Note:
compared with the blank group, **P < 0.01; and compared with the model group, ##P < 0.01.

As can be seen from table 4, the biological representation scoring experiment results of the rats in each group show that the rats in the blank control group are active and responsive; the rats in the qi-deficiency model group are lassitude, listless, sluggish and even squint; with flabby skin and matt hair on the back; with slightly white and dry tail and nose; and have loose but formed stool. Compared with the blank control group, the biological representation score is remarkably increased (P<0.01); and the biological representation scores of the rats administered with the solid beverage particles of embodiments 1-5 of the present application are significantly different (P<0.01 or P<0.05) from that of the model group.

5. In this experiment, the exhaustive swimming time of the rats in each group was further measured. The time experiment results show that, compared with the blank control group, the exhaustive swimming time of the rats in the qi-deficiency model group is remarkably reduced and has a statistically significant difference (P<0.01); and compared with the qi-deficiency model group, the exhaustive swimming time of the rats in the experimental groups of embodiments 1-5 of the present invention is remarkably increased and has a statistically significant difference (P<0.01).

6. In this experiment, hemorrheological index was further tested for the rats in each group. The experimental results show that, compared with the model group, high shear blood viscosity, middle shear blood viscosity, low shear blood viscosity, plasma viscosity, fibrinogen, and erythrocyte deformation index and aggregation index in the experimental groups of embodiments 1-5 of the present invention have been improved to different extents (P<0.01 or P<0.05).

The descriptions above are only preferred embodiments of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

What is claimed is:

1. A solid beverage for conditioning qi deficiency constitution, comprising: 25-60 parts by weight of *polygonatum odoratum,* 30-52 parts by weight of fuling, 28-53 parts by weight of Chinese dates, 26-48 parts by weight of arillus longan, 15-34 parts by weight of orange peels, 30-53 parts by weight of *lilium brownii,* 27-52 parts by weight of Chinese yam, 26-56 parts by weight of hyacinth bean, 37-77 parts by weight of dextrin, 15-43 parts by weight of maltodextrin, 18-50 parts by weight of soluble starch and 0.1-0.38 parts by weight of aspartame.

2. The solid beverage for conditioning qi deficiency constitution according to claim 1, wherein the *polygonatum odoratum* is 35-50 parts by weight, the fuling is 35-45 parts by weight, the Chinese dates are 33-47 parts by weight, the arillus longan is 30-43 parts by weight, the orange peels are 20-29 parts by weight, the *lilium brownii* is 36-48 parts by weight, the Chinese yam is 33-44 parts by weight, the hyacinth beans are 31-50 parts by weight, the dextrin is 45-65 parts by weight, the maltodextrin is 20-35 parts by weight, the soluble starch is 22-35 parts by weight and the aspartame is 0.15-0.33 parts by weight.

3. The solid beverage for conditioning qi deficiency constitution according to claim 1, wherein the *polygonatum odoratum* is 40 parts by weight, the fuling is 40 parts by weight, the Chinese dates are 40 parts by weight, the arillus longan is 40 parts by weight, the orange peels are 24 parts by weight, the *lilium brownii* is 40 parts by weight, the Chinese yam is 40 parts by weight, the hyacinth beans are 40 parts by weight, the dextrin is 55 parts by weight, the maltodextrin is 28 parts by weight, the soluble starch is 28 parts by weight and the aspartame is 0.22 parts by weight.

* * * * *